(12) United States Patent
Nakajima et al.

(10) Patent No.: US 9,498,810 B2
(45) Date of Patent: Nov. 22, 2016

(54) METHOD FOR MANUFACTURING WARM PRESSED-FORMED MEMBERS

(75) Inventors: Seiji Nakajima, Chiba (JP); Tatsuya Miyoshi, Fukuyama (JP); Hiroki Nakamaru, Fukuyama (JP)

(73) Assignee: JFE Steel Corporation, Tokyo (JP)

( * ) Notice: Subject to any disclaimer, the term of this patent is extended or adjusted under 35 U.S.C. 154(b) by 413 days.

(21) Appl. No.: 13/991,055

(22) PCT Filed: Nov. 30, 2011

(86) PCT No.: PCT/JP2011/078225
§ 371 (c)(1),
(2), (4) Date: Sep. 6, 2013

(87) PCT Pub. No.: WO2012/074132
PCT Pub. Date: Jun. 7, 2012

(65) Prior Publication Data
US 2013/0333436 A1   Dec. 19, 2013

(30) Foreign Application Priority Data

Dec. 3, 2010 (JP) ................................. 2010-269851
Jan. 5, 2011 (JP) ................................. 2011-000555
Apr. 18, 2011 (JP) ................................. 2011-091635
Jul. 26, 2011 (JP) ................................. 2011-162679

(51) Int. Cl.
| | |
|---|---|
| B21D 22/02 | (2006.01) |
| B32B 15/01 | (2006.01) |
| C21D 9/46 | (2006.01) |
| C22C 18/00 | (2006.01) |

(Continued)

(52) U.S. Cl.
CPC ............ *B21D 22/022* (2013.01); *B32B 15/013* (2013.01); *B32B 15/015* (2013.01); *C21D 9/46* (2013.01); *C22C 18/00* (2013.01); *C22C 38/001* (2013.01); *C22C 38/02* (2013.01); *C22C 38/04* (2013.01); *C22C 38/06* (2013.01); *C22C 38/12* (2013.01); *C22C 38/14* (2013.01); *C23C 2/06* (2013.01); *C23C 2/28* (2013.01);

(Continued)

(58) Field of Classification Search
CPC .... B21D 22/022; C21D 9/46; B23B 15/013; C22C 18/00
See application file for complete search history.

(56) References Cited

U.S. PATENT DOCUMENTS

2004/0166360 A1*  8/2004  Imai et al. .................... 428/658

FOREIGN PATENT DOCUMENTS

| | | |
|---|---|---|
| CN | 100434564 | 11/2008 |
| EP | 1439240 | 7/2004 |

(Continued)

OTHER PUBLICATIONS

Machine Translation of JP 2005-113233 A, Maki et al., pp. 1-11.*

(Continued)

*Primary Examiner* — Teresa M Ekiert
(74) *Attorney, Agent, or Firm* — RatnerPrestia (57) ABSTRACT

The invention provides methods for manufacturing warm press-formed members which can ensure post-coating corrosion resistance. A method for manufacturing warm press-formed members includes heating a steel sheet to a temperature in the range from 200 to 800° C. and warm press-forming the steel sheet at a temperature in the above range of temperatures, the steel sheet having a Zn—Ni alloy coating layer on its surface, the coating layer including 10 to 25 mass % Ni and the balance being Zn and inevitable impurities and having a coating weight of 10 to 90 g/m$^2$.

3 Claims, 1 Drawing Sheet

(51) Int. Cl.

| | | |
|---|---|---|
| C23C 2/06 | (2006.01) | |
| C23C 2/28 | (2006.01) | |
| C25D 5/50 | (2006.01) | |
| C22C 38/12 | (2006.01) | |
| C22C 38/00 | (2006.01) | |
| C22C 38/02 | (2006.01) | |
| C22C 38/04 | (2006.01) | |
| C22C 38/06 | (2006.01) | |
| C22C 38/14 | (2006.01) | |
| C21D 1/673 | (2006.01) | |
| G01N 19/02 | (2006.01) | |

(52) U.S. Cl.
    CPC .............. *C25D 5/50* (2013.01); *C21D 1/673* (2013.01); *G01N 19/02* (2013.01)

(56) References Cited

FOREIGN PATENT DOCUMENTS

| JP | 3-47987 A | 2/1991 |
|---|---|---|
| JP | 2000-15741 A | 1/2000 |
| JP | 2000-234153 A | 8/2000 |
| JP | 2001-314923 A | 11/2001 |
| JP | 2003-73774 A | 3/2003 |
| JP | 2003-129209 A | 5/2003 |
| JP | 2005-113233 A | 4/2005 |
| JP | 2007063578 | 3/2007 |
| JP | 2007-308744 A | 11/2007 |
| JP | 2010-90462 A | 4/2010 |
| JP | 2010-90463 A | 4/2010 |
| JP | 2010-90464 A | 4/2010 |
| JP | 2010-242196 A | 10/2010 |

OTHER PUBLICATIONS

International Search Report dated Feb. 14, 2012, application No. PCT/JP2011/078225.

Chinese Office Action dated May 5, 2016 for Chinese Application No. 201180057971.4, including Concise Statement of Relevance, 19 pages.

\* cited by examiner

SAMPLE SLIDING DIRECTION

METHOD FOR MANUFACTURING WARM PRESSED-FORMED MEMBERS

CROSS REFERENCE TO RELATED APPLICATIONS

This application is the U.S. National Phase application of PCT/JP2011/078225, filed Nov. 30, 2011, and claims priority to Japanese Patent Application No. 2010-269851, filed Dec. 3, 2010, Japanese Patent Application No. 2011-000555, filed Jan. 5, 2011, Japanese Patent Application No. 2011-091635, filed Apr. 18, 2011, and Japanese Patent Application No. 2011-162679, filed Jul. 26, 2011, the disclosures of each of these applications being incorporated herein by reference in their entireties for all purposes.

FIELD OF THE INVENTION

The present invention relates to methods for manufacturing warm press-formed members suited for producing components such as automobile chassis and car body structural components.

BACKGROUND OF THE INVENTION

Many of components such as automobile chassis and car body structural components are conventionally produced by press-forming steel sheets having prescribed strength. In recent years, great demands have been placed on reducing the weight of automobile bodies from the viewpoint of global environment preservation. Thus, efforts are under way to increase the strength of steel sheets used and thereby reduce the sheet thickness. However, increasing the strength of steel sheets is accompanied by a decrease in press foamability of the steel sheets. As a result, difficulties are more frequently encountered in forming steel sheets into a shape of desired members.

Thus, attentions have been drawn to a technique in which steel sheets are press formed after being heated beforehand. In particular, warm press-forming is a technique in which steel sheets are press formed after being heated to a relatively low temperature. As compared with cold press-forming techniques, the warm press-forming technique allows a decrease in forming load as well as improvements in formability such as stretch flangeability and shape fixability. With these advantages, a variety of warm press-forming methods have been proposed.

For example, Patent Literature 1 proposes a method for manufacturing high-strength, press-formed products which includes heating a hot-rolled, cold-rolled or Zn-coated steel sheet containing prescribed components to a temperature of 200 to 850° C., and thereafter warm forming the steel sheet at the temperature such that a plastic strain of not less than 2% is applied to a region which requires strength so as to ensure a ratio of an increase in tensile strength exceeding 1.10.

Patent Literature 2 proposes a method for warm press-forming high-strength steel sheets in which a high-strength steel sheet is successively press formed at high speed through multistage steps. In this method, the high-strength steel sheet is rapidly heated between steps in the course of press-forming.

Further, Patent Literature 3 proposes a method for manufacturing high-strength, warm press-formed members which includes plastically deforming a high-strength steel sheet with a tensile strength of not less than 980 MPa to form a plastically deformed region with a logarithmic strain of not less than 1 in the entirety or a portion of the high-strength steel sheet, and press-forming the steel sheet at a temperature in a warm temperature range to produce a high-strength, warm press-formed member.

Meanwhile, corrosion resistance has recently become of greater interest also for components such as automobile chassis and car body structural components. In particular, there has been an increasing demand that the occurrence of blisters at flaws after coating be suppressed, namely, post-coating corrosion resistance be exhibited.

PATENT LITERATURE

[PTL 1] Japanese Patent No. 3962186
[PTL 2] Japanese Unexamined Patent Application Publication No. 2001-314923
[PTL 3] Japanese Unexamined Patent Application Publication No. 2007-308744

SUMMARY OF THE INVENTION

Warm press-formed members obtained by the warm press-forming methods described in Patent Literatures 1 to 3 are poor in post-coating corrosion resistance. It is very difficult to reliably ensure post-coating corrosion resistance even when Zn-coated steel sheets disclosed in the above literatures are used.

The present invention provides methods for manufacturing warm press-formed members which can ensure post-coating corrosion resistance.

The present inventors diligently studied methods for the manufacturing of warm press-formed members to achieve the above object. As a result, the present inventors have found the following.

i) It is difficult to ensure post-coating corrosion resistance even when Zn-coated steel sheets disclosed in Patent Literatures 1 and 2 are used. The reason for this is because during heating before warm press-forming, zinc in the coating layer forms a large amount of zinc oxide on the surface of the coating layer, or is diffused into the base steel sheet and some of such zinc form a Zn—Fe intermetallic compound, with the result that the inherent sacrificial anticorrosive effect of zinc is markedly lowered.

ii) In order to suppress the formation of a large amount of zinc oxide on the surface of the coating layer or to suppress the diffusion of zinc into the base steel sheet, it is effective to provide a Zn—Ni alloy coating layer including 10 to 25 mass % Ni and the balance being Zn and inevitable impurities.

iii) The diffusion of zinc into the base steel sheet can be suppressed more effectively and the post-coating corrosion resistance can be effectively further enhanced by providing a lower coating layer including not less than 60 mass % Ni and the balance being Zn and inevitable impurities between the base steel sheet and the Zn—Ni alloy coating layer.

The present invention has been made based on the above findings. The present invention provides a method for manufacturing warm press-formed members including heating a steel sheet to a temperature in the range from 200 to 800° C. and warm press-forming the steel sheet at a temperature in the above range of temperatures, the steel sheet having a Zn—Ni alloy coating layer on the surface of the steel sheet which includes 10 to 25 mass % Ni and the balance being Zn and inevitable impurities and has a coating weight of 10 to 90 g/m$^2$.

Further, the present invention provides a method for manufacturing warm press-formed members including heating a steel sheet to a temperature in the range from 200 to 800° C. and warm press-forming the steel sheet at a temperature in the above range of temperatures, the steel sheet having a lower coating layer and a Zn—Ni alloy coating layer in this order on the surface of the steel sheet, the lower coating layer including not less than 60 mass % Ni and the balance being Zn and inevitable impurities and having a coating weight of 0.01 to 5 g/m$^2$, the Zn—Ni alloy coating layer including 10 to 25 mass % Ni and the balance being Zn and inevitable impurities and having a coating weight of 10 to 90 g/m$^2$.

In the inventive methods for manufacturing warm press-formed members, it is preferable that the steel sheet used further has, on the Zn—Ni alloy coating layer, at least one compound layer selected from Si-containing compound layers, Ti-containing compound layers, Al-containing compound layers and Zr-containing compound layers. These compound layers may further contain an inorganic solid lubricant.

The methods for manufacturing warm press-formed members of the present invention make it possible to manufacture warm press-formed members which can ensure post-coating corrosion resistance. Warm press-formed members manufactured by the inventive methods for manufacturing warm press-formed members are suited for automobile chassis and car body structural components.

DETAILED DESCRIPTION OF EMBODIMENTS OF THE INVENTION

1) Steel Sheets to be Warm Press-Formed
1-1) Coating Layer

In order to ensure post-coating corrosion resistance due to the sacrificial anticorrosive effect of zinc by suppressing the formation of zinc oxide on the surface of a coating layer as well as by suppressing the diffusion of zinc in the coating layer into a base steel sheet, the present invention provides that a Zn—Ni alloy coating layer is disposed, on the surface of a steel sheet, that includes 10 to 25 mass % Ni and the balance being Zn and inevitable impurities. Limiting the Ni content in the Zn—Ni alloy coating layer in the range from 10 to 25 mass % ensures that a γ-phase is formed which has a crystal structure represented by any of $Ni_2Zn_{11}$, $NiZn_3$ and $Ni_5Zn_{21}$ and exhibits as high a melting point as 881° C. Consequently, a zinc oxide-forming reaction on the surface of the coating layer during a heating process is suppressed to a minimum extent. The coating layer having such a melting point ensures that the diffusion of zinc into the base steel sheet during a heating process is suppressed to a minimum extent and the content of Zn present in the coating layer can be maintained at a high level even after heating, thus making it possible to obtain excellent post-coating corrosion resistance utilizing the sacrificial anticorrosive effect of zinc.

The formation of γ-phase with the Ni content of 10 to 25 mass % is not necessarily consistent with the equilibrium diagram of the Ni—Zn alloy. This inconsistency probably arises because the reaction forming a coating layer by a method such as electroplating does not take place in equilibrium. The γ-phase of $Ni_2Zn_{11}$, $NiZn_3$ or $Ni_5Zn_{21}$ can be identified by an X-ray diffraction method or an electron diffraction method using TEM (transmission electron microscopy).

The coating weight of the Zn—Ni alloy coating layer on each surface is limited to be 10 to 90 g/m$^2$. If the coating weight is less than 10 g/m$^2$, post-coating corrosion resistance is not improved sufficiently. If the coating weight exceeds 90 g/m$^2$, the improvement effect is saturated and costs are increased.

In order to obtain still higher post-coating corrosion resistance by further suppressing the diffusion of zinc in the Zn—Ni alloy coating layer into the base steel sheet, it is preferable in the invention that a lower coating layer including not less than 60 mass % Ni and the balance being Zn and inevitable impurities be provided between the base steel sheet and the Zn—Ni alloy coating layer. If the Ni content in the lower coating layer is less than 60 mass %, such a coating layer cannot suppress sufficiently the diffusion of zinc in the Zn—Ni alloy coating layer into the base steel sheet and fails to achieve a further improvement in post-coating corrosion resistance. Specifically, the Ni content is preferably 100 mass %. In the case where the Ni content is less than 100 mass %, however, the balance is Zn having a sacrificial anticorrosive effect and inevitable impurities. The coating weight of the lower coating layer on each surface is limited to be 0.01 to 5 g/m$^2$. If the coating weight is less than 0.01 g/m$^2$, such a coating layer cannot have effect on suppressing sufficiently the diffusion of zinc in the Zn—Ni alloy coating layer into the base steel sheet. If the coating weight exceeds 5 g/m$^2$, the suppressive effect is saturated and costs are increased.

The Zn—Ni alloy coating layer and the lower coating layer may be formed by any methods without limitation. However, a known electroplating method is preferable.

Excellent paint adhesion can be obtained by providing, on the Zn—Ni alloy coating layer, at least one compound layer selected from Si-containing compound layers, Ti-containing compound layers, Al-containing compound layers and Zr-containing compound layers. In order to obtain this effect, it is preferable that the thickness of the compound layer be not less than 0.1 μm. If the thickness exceeds 3.0 μm, the compound layer may become brittle and the paint adhesion may be decreased. Thus, the thickness is preferably controlled to be not more than 3.0 μl. The thickness is more preferably 0.4 to 2.0 μm.

Examples of Si-containing compounds include silicone resins, lithium silicate, sodium silicate, colloidal silica and silane coupling agents. Examples of Ti-containing compounds include titanium coupling agents based on titanates such as lithium titanate and calcium titanate, titanium alkoxides or chelated titanium compounds. Examples of Al-containing compounds include aluminum coupling agents based on aluminates such as sodium aluminate and calcium aluminate, aluminum alkoxides or chelated aluminum compounds. Examples of Zr-containing compounds include zirconium coupling agents based on zirconates such as lithium zirconate and calcium zirconate, zirconium alkoxides or chelated zirconium compounds.

Such a compound layer(s) may be formed on the Zn—Ni alloy coating layer by attaching at least one compound selected from the above Si-containing compounds, Ti-containing compounds, Al-containing compounds and Zr-containing compounds onto the coating layer, and thereafter drying the coating by heating without washing with water. These compounds may be attached by any methods such as coating, dipping and spraying, using appropriate devices such as roll coaters, squeeze coaters and die coaters. After being attached by a coating treatment with a squeeze coater or the like, a dipping treatment or a spray treatment, the compound may be treated by an air knife method or a roll squeeze method to control the coating amount and to make the appearance and the thickness uniform. The thermal drying is preferably carried out such that the maximum temperature of the steel sheet reaches 40 to 200° C., and more preferably 60 to 160° C.

Alternatively, such a compound layer(s) may be formed on the Zn—Ni alloy coating layer by subjecting the steel sheet having the coating layer to a reactive treatment in which the steel sheet is dipped into an acidic aqueous solution containing at least one cation selected from Si, Ti, Al and Zr as well as at least one anion selected from phosphate ion, fluorine acid ion and fluoride ion, and thereafter drying the steel sheet by heating after or without washing with water.

These compound layers may contain an inorganic solid lubricant. The incorporation of an inorganic solid lubricant lowers the dynamic friction coefficient during warm press-forming and thus improves press workability.

The inorganic solid lubricant may be at least one selected from metal sulfides (such as molybdenum disulfide and tungsten disulfide), selenium compounds (such as molybdenum selenide and tungsten selenide), graphites, fluorides (such as graphite fluoride and calcium fluoride), nitrides (such as boron nitride and silicon nitride), borax, mica, metallic tin and alkali metal sulfates (such as sodium sulfate and potassium sulfate). The content of these inorganic solid lubricants in the compound layer is preferably 0.1 to 20 mass %. Lubricating effects are obtained when the content is not less than 0.1 mass %. A decrease in the paint adhesion is avoided when the content is not more than 20 mass %.

1-2) Base Steel Sheets

The steel sheet as the base for the coating layer in the present invention is not particularly limited. In view of the application of the steel sheets, however, high-strength steel sheets having a tensile strength of not less than 440 MPa are desirable. It is also desirable that the base steel sheets be high-strength steel sheets that exhibit minimum changes in mechanical characteristics such as tensile strength and elongation before and after warm press-forming.

For example, the steel sheet as the base for the coating layer may be a hot-rolled steel sheet or a cold-rolled steel sheet that has a chemical composition including, by mass, 0.01 to 0.5% C, 0.01 to 2% Si, 0.1 to 3% Mn, not more than 0.1% P, not more than 0.05% S, not more than 0.1% Al and not more than 0.01% N, the balance being Fe and inevitable impurities. The reasons why the each element of the chemical composition is limited will be described below. Here, the unit "%" for the contents of elements indicates "mass %" unless otherwise mentioned.

C: 0.01 to 0.5%

Carbon is an effective element for increasing the strength of steel sheets. This effect cannot be obtained if the C content is less than 0.01%. If the C content exceeds 0.5%, formability is deteriorated. Thus, the C content is limited to be 0.01 to 0.5%.

Si: 0.01 to 2%

Silicon is an effective element for increasing the strength of steel sheets. This effect cannot be obtained if the Si content is less than 0.01%. If the Si content exceeds 2%, formability is deteriorated. Thus, the Si content is limited to be 0.01 to 2%.

Mn: 0.1 to 3%

Manganese is an effective element for increasing the strength of steel sheets. This effect cannot be obtained if the Mn content is less than 0.1%. If the Mn content exceeds 3%, formability is deteriorated. Thus, the Mn content is limited to be 0.1 to 3%.

P: not more than 0.1%

Any P content in excess of 0.1% causes deteriorations in the uniformity in mechanical characteristics due to segregation, and also leads to a marked decrease in toughness. Thus, the P content is limited to be not more than 0.1%.

S: not more than 0.05%

Hot shortness may occur if the S content exceeds 0.05%. Thus, the S content is limited to be not more than 0.05%.

Al: not more than 0.1%

The blankability of steel sheets as materials is deteriorated if the Al content exceeds 0.1%. Thus, the Al content is limited to be not more than 0.1%.

N: not more than 0.01%

If the N content exceeds 0.01%, the nitride AlN is formed during hot rolling and the blankability of steel sheets as materials is deteriorated. Thus, the N content is limited to be not more than 0.01%.

The balance is Fe and inevitable impurities. For the reasons described below, it is preferable that the steel sheet contain at least one selected from 0.01 to 2% Cr, 0.005 to 2% Ti, 0.005 to 2% Nb, 0.005 to 2% V, 0.005 to 2% Mo, 0.005 to 2% W, 0.0005 to 0.08% B and 0.003 to 0.03% Sb.

Cr: 0.01 to 2%

Chromium is an effective element for increasing the strength of steel sheets. This effect cannot be obtained if the Cr content is less than 0.01%. If the Cr content exceeds 2%, formability is deteriorated. Thus, the Cr content is preferably limited to be 0.01 to 2%.

Ti: 0.005 to 2%

Titanium is an effective element for increasing the strength of steel sheets as well as for increasing toughness by reducing grain sizes. These effects cannot be obtained if the Ti content is less than 0.005%. If the Ti content exceeds 2%, formability is deteriorated. Thus, the Ti content is preferably limited to be 0.005 to 2%.

Nb: 0.005 to 2%

Niobium is an effective element for increasing the strength of steel sheets as well as for increasing toughness by reducing grain sizes. These effects cannot be obtained if the Nb content is less than 0.005%. If the Nb content exceeds 2%, formability is deteriorated. Thus, the Nb content is preferably limited to be 0.005 to 2%.

V: 0.005 to 2%

Vanadium is an effective element for increasing the strength of steel sheets as well as for increasing toughness by reducing grain sizes. These effects cannot be obtained if the V content is less than 0.005%. If the V content exceeds 2%, formability is deteriorated. Thus, the V content is preferably limited to be 0.005 to 2%.

Mo: 0.005 to 2%

Molybdenum is an effective element for increasing the strength of steel sheets as well as for increasing toughness by reducing grain sizes. These effects cannot be obtained if the Mo content is less than 0.005%. If the Mo content exceeds 2%, formability is deteriorated. Thus, the Mo content is preferably limited to be 0.005 to 2%.

W: 0.005 to 2%

Tungsten is an effective element for increasing the strength of steel sheets as well as for increasing toughness by reducing grain sizes. These effects cannot be obtained if the W content is less than 0.005%. If the W content exceeds 2%, formability is deteriorated. Thus, the W content is preferably limited to be 0.005 to 2%.

B: 0.0005 to 0.08%

Boron is an effective element for increasing the toughness of steel sheets. This effect cannot be obtained if the B content is less than 0.0005%. If the B content exceeds 0.08%, hot rolling of such steel sheets incurs an extremely high rolling load and may result in the occurrence of cracks. Thus, the B content is preferably limited to be 0.0005 to 0.08%.

Sb: 0.003 to 0.03%

Antimony has an effect of suppressing the formation of decarburized layer at a surface portion during heating of steel sheets. This effect cannot be obtained if the Sb content is less than 0.003%. Any Sb content in excess of 0.03% causes an increase in rolling load and a deterioration in productivity. Thus, the Sb content is preferably limited to be 0.003 to 0.03%.

2) Warm Press-Forming Methods

In the present invention, the aforementioned steel sheet to be warm press-formed is preferably heated to a temperature in the range from 200 to 800° C. and is thereafter warm press-formed at a temperature in the above range of temperatures. Heating of the steel sheet to a temperature in the range from 200 to 800° C. before press-forming makes it possible to reduce forming load as well as to improve formability such as stretch flangeability and shape fixability. The steel sheet needs to be heated to not less than 200° C. because the above effects are poor if the heating temperature is less than 200° C. On the other hand, energy costs are increased if the heating temperature exceeds 800° C. Thus, the heating temperature for the steel sheet is limited to be 200 to 800° C., and preferably 200 to 700° C. For the same reasons why the heating temperature before press-forming is limited as described above, the temperature of the steel sheet during warm press-forming needs to be 200 to 800° C., and preferably 200 to 700° C. In the case where the steel sheet is heated before press-forming and is warm press-formed with different apparatuses, the transportation between the apparatuses needs to complete as quickly as possible. The transportation time is limited to be not more than 20 seconds, more preferably not more than 10 seconds, and still more preferably not more than 5 seconds.

The heating rate at which the steel sheet is heated to the heating temperature, and the cooling rate after warm press-forming are not particularly limited because these rates have little influences on the mechanical characteristics and the post-coating corrosion resistance of the warm press-formed members. The holding time during heating is not particularly limited. Because prolonged heating is economically disadvantageous, however, the holding time is preferably limited to be not more than 10 seconds, and more preferably 0 seconds. Exemplary methods for heating the steel sheets include heating with a furnace such as an electric furnace or a gas furnace, flame heating, electrical heating, high frequency heating and induction heating.

Example 1

Hot-rolled steel sheets with a thickness of 2.3 mm were used as base steel sheets. The steel sheets had a chemical composition including, by mass, 0.10% C, 0.02% Si, 1.2% Mn, 0.01% P, 0.003% S, 0.03% Al, 0.003% N, 0.12% Ti and 0.22% Mo, the balance being Fe and inevitable impurities. The steel sheets were electroplated in a plating bath containing 200 g/L of nickel sulfate hexahydrate and 10 to 100 g/L of zinc sulfate heptahydrate at a pH of 1.5 and a temperature of 50° C. while changing the current density in the range from 5 to 100 A/dm$^2$. Thus, Zn—Ni alloy coating layers with different Ni contents and different coating weights were formed on the surfaces of the hot-rolled steel sheets. Before the formation of the Zn—Ni alloy coating layer, some of the steel sheets were electroplated in a plating bath containing 200 g/L of nickel sulfate hexahydrate and 0 to 50 g/L of zinc sulfate heptahydrate at a pH of 3.0 and a temperature of 50° C. while changing the current density in the range from 5 to 100 A/dm$^2$, thereby forming lower coating layers having different Ni contents and different coating weights.

The steel sheets thus obtained were heated to a heating temperature of 200 to 800° C. with use of an electric furnace. Immediately thereafter, the steel sheets were removed from the electric furnace and were cooled to room temperature by being sandwiched between Al dies. In addition, a hot dip galvanized steel sheet (GI) and a galvannealed steel sheet (GA) were heat-treated in the similar manner for comparison. Table 1 describes the Ni contents and the coating weights of the lower coating layers and the Zn—Ni alloy coating layers, as well as the heating temperatures.

After these steel sheets were chemically converted and electrodeposition coated, their post-coating corrosion resistance was tested. The chemical conversion treatment was performed under standard conditions using PB-L3020 manufactured by Nihon Parkerizing Co., Ltd. The electrodeposition coating was carried out under such conditions that GT-10 manufactured by Kansai Paint Co., Ltd. was deposited at a voltage of 200 V and was thereafter baked at 170° C. for 20 minutes. To test the post-coating corrosion resistance, the electrodeposition coated sample was cross cut with a cutter knife to a depth reaching the base steel sheet. The surface and edges which were free from the cross cut marks were sealed. Thereafter, the sample was subjected to a salt spraying test for 480 hours in accordance with JIS Z2371-2000, and was washed with water and dried. A cellophane adhesive tape was applied to and peeled from the cross cut section. The maximum peel width from any one cut line in the cross cut section was measured and was evaluated as follows. Steel sheets evaluated with ⊙ and ○ were assessed to satisfy the object of the present invention.

⊙: Maximum peel width from any one cut line≤3 mm

○: 3 mm<Maximum peel width from any one cut line≤4 mm x: 4 mm<Maximum peel width from any one cut line Table 1 describes the results of the evaluation of post-coating corrosion resistance. It has been demonstrated that all the steel sheets of Inventive Examples exhibited excellent post-coating corrosion resistance.

Although warm press-forming was not actually performed in this example, the results in this example allow the evaluation of post-coating corrosion resistance of warm press-formed members because, as described hereinabove, post-coating corrosion resistance is affected by changes of coating layers due to heating before warm press-forming, in particular by the behavior of zinc in coating layers.

TABLE 1

| Steel sheet No. | Lower coating layer Ni content (mass %) | Lower coating layer Coating weight (g/m²) | Zn—Ni alloy coating layer Ni content (mass %) | Zn—Ni alloy coating layer Coating weight (g/m²) | Heating temp. (° C.) | Post-coating corrosion resistance Max. peel width (mm) | Eval. | Remarks |
|---|---|---|---|---|---|---|---|---|
| 1 | — | — | 12 | 45 | 600 | 2.5 | ⊙ | Inv. Ex. |
| 2 | — | — | 10 | 45 | 600 | 3.5 | ○ | Inv. Ex. |
| 3 | — | — | 18 | 45 | 600 | 2.5 | ⊙ | Inv. Ex. |
| 4 | — | — | 25 | 45 | 600 | 3.0 | ⊙ | Inv. Ex. |
| 5 | — | — | 12 | 10 | 600 | 3.5 | ○ | Inv. Ex. |
| 6 | — | — | 12 | 30 | 600 | 3.0 | ⊙ | Inv. Ex. |
| 7 | — | — | 12 | 60 | 600 | 2.0 | ⊙ | Inv. Ex. |
| 8 | — | — | 12 | 90 | 600 | 1.5 | ⊙ | Inv. Ex. |
| 9 | — | — | 12 | 45 | 200 | 1.5 | ⊙ | Inv. Ex. |
| 10 | — | — | 12 | 45 | 400 | 2.0 | ⊙ | Inv. Ex. |
| 11 | — | — | 12 | 45 | 800 | 3.5 | ○ | Inv. Ex. |
| 12 | 100 | 0.05 | 12 | 45 | 600 | 2.0 | ⊙ | Inv. Ex. |
| 13 | 100 | 0.05 | 10 | 45 | 600 | 3.0 | ⊙ | Inv. Ex. |
| 14 | 100 | 0.05 | 18 | 45 | 600 | 2.0 | ⊙ | Inv. Ex. |
| 15 | 100 | 0.05 | 25 | 45 | 600 | 2.5 | ⊙ | Inv. Ex. |
| 16 | 100 | 0.05 | 12 | 10 | 600 | 3.0 | ⊙ | Inv. Ex. |
| 17 | 100 | 0.05 | 12 | 30 | 600 | 2.5 | ⊙ | Inv. Ex. |
| 18 | 100 | 0.05 | 12 | 60 | 600 | 1.5 | ⊙ | Inv. Ex. |
| 19 | 100 | 0.05 | 12 | 90 | 600 | 1.0 | ⊙ | Inv. Ex. |
| 20 | 100 | 0.05 | 12 | 45 | 200 | 1.0 | ⊙ | Inv. Ex. |
| 21 | 100 | 0.05 | 12 | 45 | 400 | 1.5 | ⊙ | Inv. Ex. |
| 22 | 100 | 0.05 | 12 | 45 | 800 | 3.0 | ⊙ | Inv. Ex. |
| 23 | 60 | 0.05 | 12 | 45 | 600 | 2.2 | ⊙ | Inv. Ex. |
| 24 | 100 | 0.01 | 12 | 45 | 600 | 2.3 | ⊙ | Inv. Ex. |
| 25 | 100 | 0.5 | 12 | 45 | 600 | 1.8 | ⊙ | Inv. Ex. |
| 26 | 100 | 5 | 12 | 45 | 600 | 1.5 | ⊙ | Inv. Ex. |
| 27 | — | — | 9 | 45 | 600 | 4.5 | X | Comp. Ex. |
| 28 | — | — | 26 | 45 | 600 | 4.5 | X | Comp. Ex. |
| 29 | — | — | 12 | 9 | 600 | 4.5 | X | Comp. Ex. |
| 30 | — | — | GI | 60 | 600 | 6.0 | X | Comp. Ex. |
| 31 | — | — | GA | 45 | 600 | 5.5 | X | Comp. Ex. |

Example 2

Base steel sheets similar to those used in EXAMPLE 1 were treated in the same manner as in EXAMPLE 1 to form Zn—Ni alloy coating layers with different Ni contents and different coating weights on the surfaces of the steel sheets. Before this formation of the Zn—Ni alloy coating layer, some of the steel sheets were electroplated in the same manner as in EXAMPLE 1 to form lower coating layers having different Ni contents and different coating weights. Thereafter, a composition (solid content 15 mass %) containing any one of the following Si-containing compounds, Ti-containing compounds, Al-containing compounds, Zr-containing compounds, and Si- and Zr-containing compounds, the balance being a solvent, was applied onto the Zn—Ni alloy coating layer and was dried under such conditions that the steel sheet temperature reached 140° C. Thus, steel sheets Nos. 1 to 42 were produced which had any one of Si-containing compound layers, Ti-containing compound layers, Al-containing compound layers, Zr-containing compound layers, and Si- and Zr-containing compound layers with different thicknesses described in Tables 2 and 3.

The Si-containing compounds, Ti-containing compounds, Al-containing compounds and Zr-containing compounds used herein are the following compounds.

Silicone resin: KR-242A manufactured by Shin-Etsu Chemical Co., Ltd.

Lithium silicate: lithium silicate 45 manufactured by NISSAN CHEMICAL INDUSTRIES, LTD.

Colloidal silica: SNOWTEX OS manufactured by NISSAN CHEMICAL INDUSTRIES, LTD.

Silane coupling agent: KBE-403 manufactured by Shin-Etsu Chemical Co., Ltd.

Titanium coupling agent: ORGATIX TA-22 manufactured by Matsumoto Fine Chemical Co., Ltd.

Lithium titanate: lithium titanate manufactured by Titan Kogyo, Ltd.

Sodium aluminate: NA-170 manufactured by Asahi Chemical Co., Ltd.

Aluminum coupling agent: PLENACT AL-M manufactured by Ajinomoto Fine-Techno Co., Inc.

Zirconium acetate: zirconium acetate manufactured by SAN'EI KAKO CO., LTD.

Zirconium coupling agent: ORGATIX ZA-65 manufactured by Matsumoto Fine Chemical Co., Ltd.

Thinner containing ethylene glycol monobutyl ether and petroleum naphtha in a ratio of 55:45 (by mass) was used as the solvent for the silicone resin. For the compounds other than the silicone resin, deionized water was used as the solvent.

The steel sheets thus obtained were heated to a heating temperature of 200 to 800° C. with use of an electric furnace. Immediately thereafter, the steel sheets were removed from the electric furnace and were cooled to room temperature by being sandwiched between Al dies. Tables 2 and 3 describe the Ni contents and the coating weights of the lower coating layers and the Zn—Ni alloy coating layers, as well as the compounds forming the compound layers, the thicknesses of the compound layers and the heating temperatures.

These steel sheets were tested in the same manner as in EXAMPLE 1 to evaluate their post-coating corrosion resistance. Further, the paint adhesion was evaluated in the following manner. Paint adhesion: A sample was obtained from the heat-treated steel sheet and was subjected to a chemical conversion treatment under standard conditions using PB-SX35 manufactured by Nihon Parkerizing Co., Ltd. Thereafter, electrodeposition paint GT-10HT Gray manufactured by Kansai Paint Co., Ltd. was deposited and baked at 170° C. for 20 minutes to form a coating film with a film thickness of 20 thereby producing a coated test piece. The surface of the test piece which had been subjected to the chemical conversion treatment and the electrodeposition coating was cut with a cutter knife to a depth reaching the base steel so as to form a lattice pattern (10×10 squares with 1 mm intervals). An adhesive tape was applied to and peeled from the lattice pattern. The results of this cross-cut adhesion test were evaluated on the basis of the following criteria. The symbols ⊙ and ◯ indicate that the paint adhesion was excellent.

⊙: No peeling
◯: Peeling at 1 to 10 squares
Δ: Peeling at 11 to 30 squares
x: Peeling at 31 or more squares The results are described in Tables 2 and 3. It has been illustrated that the incorporation of the compound layers provided not only excellent post-coating corrosion resistance but also excellent paint adhesion.

TABLE 2

| Steel sheet No. | Lower coating layer Ni content (mass %) | Lower coating layer Coating weight (g/m²) | Zn—Ni alloy coating layer Ni content (mass %) | Zn—Ni alloy coating layer Coating weight (g/m²) | Si, Ti, Al and Zr compound layers Compound | Si, Ti, Al and Zr compound layers Thickness (μm) | Heating temp. (° C.) | Post-coating corrosion resistance Max. peel width (mm) | Post-coating corrosion resistance Eval. | Paint adhesion | Remarks |
|---|---|---|---|---|---|---|---|---|---|---|---|
| 1 | — | — | 12 | 45 | Silicone resin | 0.5 | 600 | 2.2 | ⊙ | ⊙ | Inv. Ex. |
| 2 | — | — | 12 | 45 | Lithium silicate | 0.5 | 600 | 2.4 | ⊙ | ⊙ | Inv. Ex. |
| 3 | — | — | 12 | 45 | Colloidal silica | 0.5 | 600 | 2.8 | ⊙ | ⊙ | Inv. Ex. |
| 4 | — | — | 12 | 45 | Silane coupling agent | 0.5 | 600 | 2.3 | ⊙ | ⊙ | Inv. Ex. |
| 5 | — | — | 12 | 45 | Titanate coupling agent | 0.5 | 600 | 2.6 | ⊙ | ⊙ | Inv. Ex. |
| 6 | — | — | 12 | 45 | Lithium titanate | 0.5 | 600 | 2.6 | ⊙ | ⊙ | Inv. Ex. |
| 7 | — | — | 12 | 45 | Sodium aluminate | 0.5 | 600 | 2.7 | ⊙ | ⊙ | Inv. Ex. |
| 8 | — | — | 12 | 45 | Aluminate coupling agent | 0.5 | 600 | 2.5 | ⊙ | ⊙ | Inv. Ex. |
| 9 | — | — | 12 | 45 | Zirconium acetate | 0.5 | 600 | 2.6 | ⊙ | ⊙ | Inv. Ex. |
| 10 | — | — | 12 | 45 | Zirconate coupling agent | 0.5 | 600 | 2.2 | ⊙ | ⊙ | Inv. Ex. |
| 11 | — | — | 12 | 45 | Silane coupling agent + Zirconate coupling agent | 0.5 | 600 | 2.1 | ⊙ | ⊙ | Inv. Ex. |
| 12 | — | — | 12 | 45 | — | — | 600 | 2.5 | ⊙ | Δ | Inv. Ex. |
| 13 | — | — | 12 | 45 | Silicone resin | 0.1 | 600 | 3.5 | ⊙ | ◯ | Inv. Ex. |
| 14 | — | — | 12 | 45 | Silicone resin | 0.4 | 600 | 2.8 | ⊙ | ⊙ | Inv. Ex. |
| 15 | — | — | 12 | 45 | Silicone resin | 2.0 | 600 | 2.1 | ⊙ | ⊙ | Inv. Ex. |
| 16 | — | — | 12 | 45 | Silicone resin | 3.0 | 600 | 3.1 | ⊙ | ⊙ | Inv. Ex. |
| 17 | — | — | 12 | 45 | Silicone resin | 4.0 | 600 | 3.8 | ⊙ | ◯ | Inv. Ex. |
| 18 | — | — | 10 | 45 | Silicone resin | 0.5 | 600 | 3.7 | ⊙ | ⊙ | Inv. Ex. |
| 19 | — | — | 18 | 45 | Silicone resin | 0.5 | 600 | 2.4 | ⊙ | ⊙ | Inv. Ex. |
| 20 | — | — | 25 | 45 | Silicone resin | 0.5 | 600 | 2.9 | ⊙ | ⊙ | Inv. Ex. |
| 21 | — | — | 12 | 10 | Silicone resin | 0.5 | 600 | 3.6 | ⊙ | ◯ | Inv. Ex. |
| 22 | — | — | 12 | 30 | Silicone resin | 0.5 | 600 | 3.0 | ⊙ | ⊙ | Inv. Ex. |

TABLE 3

| Steel sheet No. | Lower coating layer Ni content (mass %) | Lower coating layer Coating weight (g/m²) | Zn—Ni alloy coating layer Ni content (mass %) | Zn—Ni alloy coating layer Coating weight (g/m²) | Si, Ti, Al and Zr compound layers Compound | Si, Ti, Al and Zr compound layers Thickness (μm) | Heating temp. (° C.) | Post-coating corrosion resistance Max. peel width (mm) | Post-coating corrosion resistance Eval. | Paint adhesion | Remarks |
|---|---|---|---|---|---|---|---|---|---|---|---|
| 23 | — | — | 12 | 60 | Silicone resin | 0.5 | 600 | 2.1 | ⊙ | ⊙ | Inv. Ex. |
| 24 | — | — | 12 | 90 | Silicone resin | 0.5 | 600 | 1.6 | ⊙ | ⊙ | Inv. Ex. |
| 25 | — | — | 12 | 45 | Silicone resin | 0.5 | 200 | 1.5 | ⊙ | ⊙ | Inv. Ex. |
| 26 | — | — | 12 | 45 | Silicone resin | 0.5 | 400 | 2.1 | ⊙ | ⊙ | Inv. Ex. |
| 27 | — | — | 12 | 45 | Silicone resin | 0.5 | 800 | 3.3 | ◯ | ⊙ | Inv. Ex. |
| 28 | 100 | 0.05 | 12 | 45 | Silicone resin | 0.5 | 600 | 1.9 | ⊙ | ⊙ | Inv. Ex. |
| 29 | 100 | 0.05 | 10 | 45 | Silicone resin | 0.5 | 600 | 2.9 | ⊙ | ⊙ | Inv. Ex. |
| 30 | 100 | 0.05 | 18 | 45 | Silicone resin | 0.5 | 600 | 2.0 | ⊙ | ⊙ | Inv. Ex. |
| 31 | 100 | 0.05 | 25 | 45 | Silicone resin | 0.5 | 200 | 2.6 | ⊙ | ⊙ | Inv. Ex. |
| 32 | 100 | 0.05 | 12 | 10 | Silicone resin | 0.5 | 400 | 3.0 | ⊙ | ◯ | Inv. Ex. |
| 33 | 100 | 0.05 | 12 | 30 | Silicone resin | 0.5 | 800 | 2.2 | ⊙ | ⊙ | Inv. Ex. |
| 34 | 100 | 0.05 | 12 | 60 | Silicone resin | 0.5 | 600 | 1.4 | ⊙ | ⊙ | Inv. Ex. |
| 35 | 100 | 0.05 | 12 | 90 | Silicone resin | 0.5 | 600 | 1.1 | ⊙ | ⊙ | Inv. Ex. |
| 36 | 100 | 0.05 | 12 | 45 | Silicone resin | 0.5 | 200 | 1.0 | ⊙ | ⊙ | Inv. Ex. |
| 37 | 100 | 0.05 | 12 | 45 | Silicone resin | 0.5 | 400 | 1.4 | ⊙ | ⊙ | Inv. Ex. |
| 38 | 100 | 0.05 | 12 | 45 | Silicone resin | 0.5 | 800 | 2.9 | ⊙ | ⊙ | Inv. Ex. |

TABLE 3-continued

| Steel sheet No. | Lower coating layer | | Zn—Ni alloy coating layer | | Si, Ti, Al and Zr compound layers | | Heating | Post-coating corrosion resistance | | Paint adhesion | Remarks |
|---|---|---|---|---|---|---|---|---|---|---|---|
| | Ni content (mass %) | Coating weight (g/m²) | Ni content (mass %) | Coating weight (g/m²) | Compound | Thickness (μm) | temp. (° C.) | Max. peel width (mm) | Eval. | | |
| 39 | 60 | 0.05 | 12 | 45 | Silicone resin | 0.5 | 600 | 2.1 | ⊙ | ⊙ | Inv. Ex. |
| 40 | 100 | 0.01 | 12 | 45 | Silicone resin | 0.5 | 600 | 2.4 | ⊙ | ⊙ | Inv. Ex. |
| 41 | 100 | 0.5 | 12 | 45 | Silicone resin | 0.5 | 600 | 1.6 | ⊙ | ⊙ | Inv. Ex. |
| 42 | 100 | 5 | 12 | 45 | Silicone resin | 0.5 | 600 | 1.4 | ⊙ | ⊙ | Inv. Ex. |

Although warm press-forming was not actually performed in this example, the results in this example allow the evaluation of the paint adhesion of warm press-formed members for the similar reason as described with respect to post-coating corrosion resistance.

Example 3

Base steel sheets similar to those used in EXAMPLE 1 were treated in the same manner as in EXAMPLE 1 to form a lower coating layer and a Zn—Ni alloy coating layer described in Table 4 in this order on the surface of the steel sheet. Thereafter, similarly to EXAMPLE 2, a composition (solid content 15 mass %) containing a silicone resin [KR-242A manufactured by Shin-Etsu Chemical Co., Ltd.] and an inorganic solid lubricant described in Table 4, the balance being a solvent, was applied onto the Zn—Ni alloy coating layer and was dried under such conditions that the steel sheet temperature reached 140° C. to form a Si-containing compound layer described in Table 4. Thus, steel sheets Nos. 1 to 17 were produced. The inorganic solid lubricants described in Table 4 are the following compounds. In some of the steel sheets, the compound layer was formed without any inorganic solid lubricant.

Molybdenum disulfide: LM-13 manufactured by DAITO CO., LTD.

Graphite: GP-60S manufactured by Hitachi Chemical Co., Ltd.

Boron nitride: FS-1 manufactured by MIZUSHIMA FERROALLOY CO., LTD.

Tungsten disulfide: Tungmic B manufactured by JAPANESE LUBRICANT CORPORATION

Molybdenum selenide: molybdenum selenide manufactured by Mitsuwa Chemicals Co., Ltd.

Graphite fluoride: CEFBON CMA manufactured by Central Glass Co., Ltd.

Borax: sodium metaborate manufactured by TAIYO CHEMICAL INDUSTRY CO., LTD.

Metallic tin: AT-Sn No. 600 manufactured by YAMAISHI METAL CO., LTD.

Mica: A-11 manufactured by YAMAGUCHI MICA CO., LTD.

Sodium sulfate: A12 manufactured by SHIKOKU CHEMICALS CORPORATION

The solvent was thinner containing ethylene glycol monobutyl ether and petroleum naphtha in a ratio of 55:45 (by mass).

The steel sheets thus obtained were heated to a heating temperature of 600° C. with use of an electric furnace. Immediately thereafter, the steel sheets were removed from the electric furnace and were cooled to room temperature by being sandwiched between Al dies. Table 4 describes the Ni contents and the coating weights of the lower coating layers and the Zn—Ni alloy coating layers, as well as the compounds and the inorganic solid lubricants forming the compound layers, the contents of the inorganic solid lubricants, the thicknesses of the compound layers and the heating temperatures.

The steel sheets obtained after electric furnace heating at 600° C. were tested in the same manner as in EXAMPLES 1 and 2 to evaluate their post-coating corrosion resistance and paint adhesion. Further, before the electric furnace heating, the steel sheets were tested in the following manner to evaluate lubricating properties.

Figure 1:
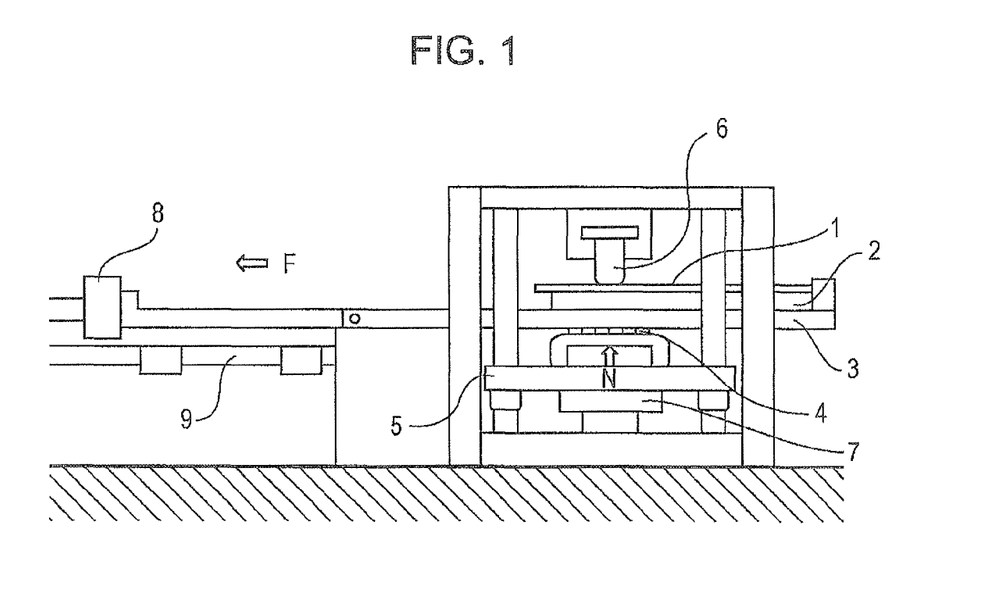
FIG. 1 is a view illustrating a friction coefficient measuring apparatus used in Examples.
Figure 2:
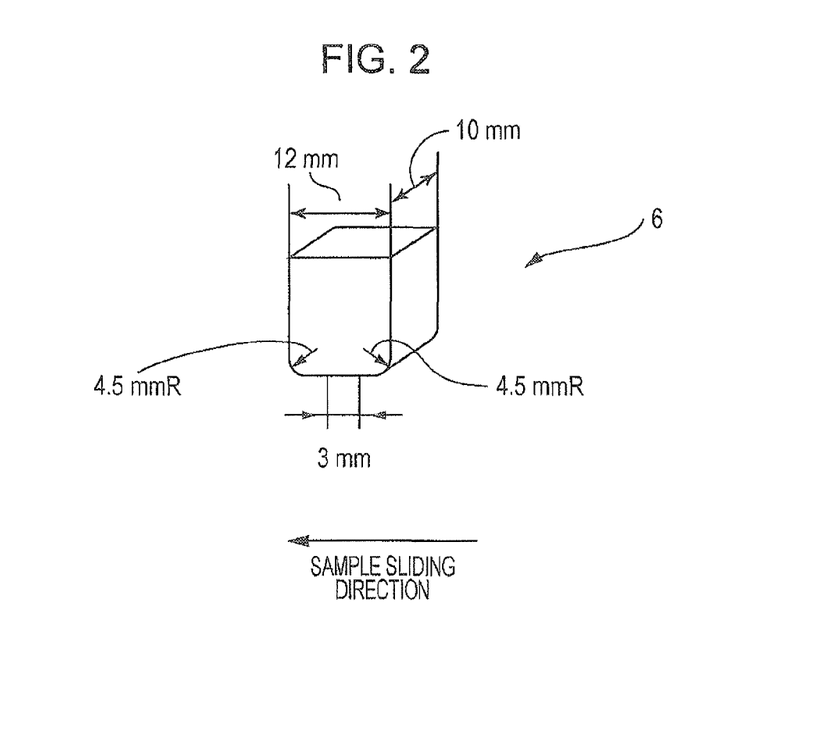
FIG. 2 is a view illustrating a shape of a bead 6 in FIG. 1.

Lubricating properties: A sample was obtained from the steel sheet before electric furnace heating. The sample was heated to 600° C. Immediately thereafter, the dynamic friction coefficient was measured in the following manner with a friction coefficient measuring apparatus illustrated in FIG. 1. As illustrated in FIG. 1, this friction coefficient measuring apparatus included a sample table 2, a slide table 3 for horizontally moving the sample table 2, rollers 4 provided under the slide table, a slide table support 5 that was located below the rollers 4 and capable of vertically moving the sample table 2, a bead 6 that was located above the sample table 2 and had a shape depicted in FIG. 2, a first load cell 7 that was fitted to the lower surface of the slide table support 5 and capable of measuring the pressure load N applied in the vertical direction, a second load cell 8 that was fitted to an end of the slide table 3 and capable of measuring the sliding frictional force F in the horizontal direction, and rails 9 on which the slide table 3 was moved horizontally. First, a sample 1 was placed on the sample table 2, and the slide table support 5 was raised until the pressure load N applied to the bead 6 by the sample 1 reached 400 kgf. Next, the slide table 3 was moved horizontally at a rate of 100 cm/min, and the sliding frictional force F was measured. The dynamic friction coefficient $\mu=F/N$ between the sample 1 and the bead 6 was determined.

The obtained coefficient μ was evaluated on the basis of the following criteria. The symbols ⊙ and ○ indicate that lubricating properties were excellent.

⊙: $\mu<0.19$
○: $0.19 \leq \mu<0.23$
Δ: $0.23 \leq \mu<0.3$
x: $0.3 \leq \mu$

The results are described in Table 4. It has been illustrated that the incorporation of the inorganic solid lubricant into the compound layer allows not only excellent post-coating corrosion resistance and paint adhesion but also excellent lubricating properties.

Although warm press-forming was not actually performed in this example, the results in this example allow the evaluation of the post-coating corrosion resistance of warm press-formed members and the paint adhesion thereof.

TABLE 4

| Steel sheet No. | Lower coating layer Ni content (mass %) | Lower coating layer Coating weight (g/m²) | Zn—Ni alloy coating layer Ni content (mass %) | Zn—Ni alloy coating layer Coating weight (g/m²) | Si compound layer Compound | Si compound layer Inorganic solid lubricant | Si compound layer Content of inorganic solid lubricant (mass %) | Si compound layer Thickness (μm) | Heating temp (°C.) | Post-coating corrosion resistance Max. peel width (mm) | Eval. | Paint adhesion | Lubricating properties | Remarks |
|---|---|---|---|---|---|---|---|---|---|---|---|---|---|---|
| 1 | 100 | 0.05 | 12 | 45 | Silicone resin | Molybdenum disulfide | 5 | 0.5 | 600 | 2.0 | ⊙ | ⊙ | ⊙ | Inv. Ex. |
| 2 | 100 | 0.05 | 12 | 45 | Silicone resin | Graphite | 5 | 0.5 | 600 | 3.2 | ○ | ⊙ | ⊙ | Inv. Ex. |
| 3 | 100 | 0.05 | 12 | 45 | Silicone resin | Boron nitride | 5 | 0.5 | 600 | 2.7 | ⊙ | ⊙ | ⊙ | Inv. Ex. |
| 4 | 100 | 0.05 | 12 | 45 | Silicone resin | Tungsten disulfide | 5 | 0.5 | 600 | 2.2 | ⊙ | ⊙ | ⊙ | Inv. Ex. |
| 5 | 100 | 0.05 | 12 | 45 | Silicone resin | Molybdenum selenide | 5 | 0.5 | 600 | 2.8 | ⊙ | ⊙ | ⊙ | Inv. Ex. |
| 6 | 100 | 0.05 | 12 | 45 | Silicone resin | Graphite fluoride | 5 | 0.5 | 600 | 2.4 | ⊙ | ⊙ | ⊙ | Inv. Ex. |
| 7 | 100 | 0.05 | 12 | 45 | Silicone resin | Borax | 5 | 0.5 | 600 | 3.0 | ⊙ | ⊙ | ⊙ | Inv. Ex. |
| 8 | 100 | 0.05 | 12 | 45 | Silicone resin | Metallic tin | 5 | 0.5 | 600 | 3.2 | ⊙ | ⊙ | ⊙ | Inv. Ex. |
| 9 | 100 | 0.05 | 12 | 45 | Silicone resin | Mica | 5 | 0.5 | 600 | 2.3 | ⊙ | ⊙ | ⊙ | Inv. Ex. |
| 10 | 100 | 0.05 | 12 | 45 | Silicone resin | Sodium sulfate | 5 | 0.5 | 600 | 3.1 | ⊙ | ⊙ | ⊙ | Inv. Ex. |
| 11 | 100 | 0.05 | 12 | 45 | Silicone resin | — | — | 0.5 | 600 | 1.9 | ⊙ | ⊙ | Δ | Inv. Ex. |
| 12 | 100 | 0.05 | 12 | 45 | Silicone resin | Molybdenum disulfide | 0.1 | 0.5 | 600 | 2.2 | ⊙ | ⊙ | ○ | Inv. Ex. |
| 13 | 100 | 0.05 | 12 | 45 | Silicone resin | Molybdenum disulfide | 1 | 0.5 | 600 | 2.3 | ⊙ | ⊙ | ○ | Inv. Ex. |
| 14 | 100 | 0.05 | 12 | 45 | Silicone resin | Molybdenum disulfide | 10 | 0.5 | 600 | 2.6 | ⊙ | ⊙ | ⊙ | Inv. Ex. |
| 15 | 100 | 0.05 | 12 | 45 | Silicone resin | Molybdenum disulfide | 20 | 0.5 | 600 | 2.8 | ⊙ | ○ | ⊙ | Inv. Ex. |
| 16 | 100 | 0.05 | 12 | 45 | Silicone resin | Molybdenum disulfide | 5 | 0.1 | 600 | 2.1 | ⊙ | ⊙ | ○ | Inv. Ex. |
| 17 | 100 | 0.05 | 12 | 45 | Silicone resin | Molybdenum disulfide | 5 | 2.0 | 600 | 1.8 | ⊙ | ○ | ⊙ | Inv. Ex. |

REFERENCE SIGNS LIST

1 SAMPLE (STEEL SHEET)
2 SAMPLE TABLE
3 SLIDE TABLE
4 ROLLERS
5 SLIDE TABLE SUPPORT
6 BEAD
7 FIRST LOAD CELL
8 SECOND LOAD CELL
9 RAILS
N PRESSURE LOAD
F SLIDING FRICTIONAL FORCE

The invention claimed is:

1. A method for manufacturing warm press-formed members, comprising heating a steel sheet to a temperature in the range from 200 to 800° C. and warm press-forming the steel sheet at a temperature in the above range of temperatures, the steel sheet having a lower coating layer and a Zn—Ni alloy coating layer in this order on the surface of the steel sheet, the lower coating layer including not less than 60 mass % Ni and the balance being Zn and inevitable impurities and having a coating weight of 0.01 to 5 g/m², the Zn—Ni alloy coating layer including 10 to 25 mass % Ni and the balance being Zn and inevitable impurities and having a coating weight of 10 to 90 g/m².

2. The method for manufacturing warm press-formed members according to claim 1, wherein the steel sheet used further has, on the Zn—Ni alloy coating layer, at least one compound layer selected from Si-containing compound layers, Ti-containing compound layers, Al-containing compound layers and Zr-containing compound layers.

3. The method for manufacturing warm press-formed members according to claim 2, wherein the compound layer contains an inorganic solid lubricant.

* * * * *